United States Patent [19]

Fix

[11] Patent Number: 4,718,462

[45] Date of Patent: Jan. 12, 1988

[54] METHOD AND APPARATUS FOR FORMING GASEOUS MIXTURES

[76] Inventor: Roger Fix, 14, boulevard du Champ de Mars, Colmar (Haut-Rhin), France

[21] Appl. No.: 226,178

[22] Filed: Jan. 19, 1981

[30] Foreign Application Priority Data

Jan. 18, 1980 [FR] France .................... 80 01366

[51] Int. Cl.$^4$ ................................ B65B 3/04
[52] U.S. Cl. ............................ 141/9; 137/7; 366/136; 366/162; 366/348
[58] Field of Search ........... 366/348, 349, 136, 137, 366/161, 138, 107, 162; 141/9, 100–110, 234–248, 392, 37–66, 1–8, 10–12; 222/3, 6, 129, 134; 48/197 R, 180; 415/116, 117; 137/7, 113

[56] References Cited

U.S. PATENT DOCUMENTS

| | | | |
|---|---|---|---|
| 1,256,673 | 2/1918 | Föttinger | 415/116 |
| 2,915,059 | 12/1959 | Masson | 128/203.14 |
| 4,206,753 | 6/1980 | Fife | 366/107 |
| 4,257,439 | 3/1981 | Mayeaux | 366/138 |
| 4,345,610 | 8/1982 | Herter et al. | 137/7 |

OTHER PUBLICATIONS

Perry, Editor, Chemical Engineers' Handbook, McGraw-Hill Book Co., Inc. (3rd Ed.), pp. 1210 and 1215 (1950).

Primary Examiner—Houston S. Bell, Jr.
Attorney, Agent, or Firm—Young & Thompson

[57] ABSTRACT

Gaseous mixtures are formed by introducing plural gases into a container with a predetermined dilution ratio of one gas in the other, withdrawing the gases from the container and admixing them in a pump, and returning the admixed gases to the container. Further dilutions according to the same or a different dilution ratio can be performed, thereby to obtain a highly dilute gas in accurately predetermined proportions. The gaseous mixtures have utility in inhalation therapy and other processes, and may for example comprise mixtures of oxygen or ammonia in diluents such as nitrogen, carbon dioxide, etc.

3 Claims, 1 Drawing Figure

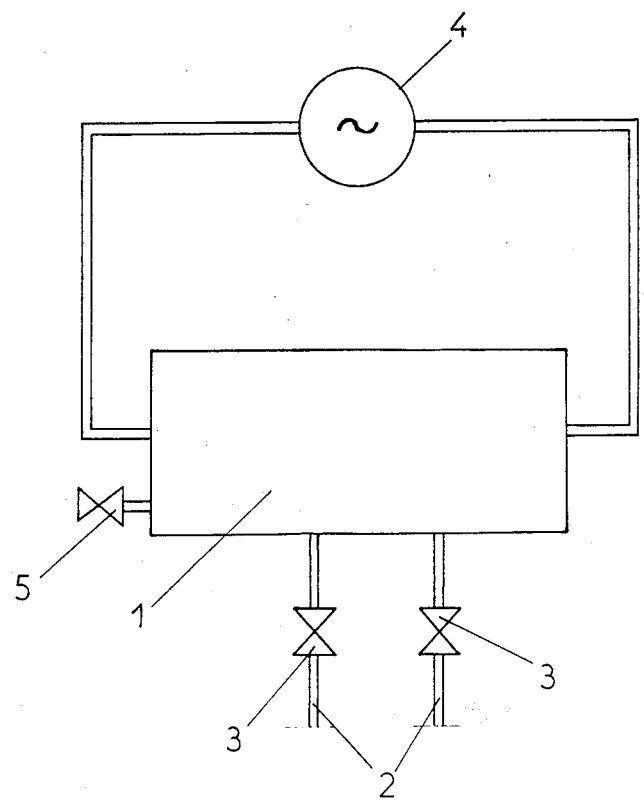

METHOD AND APPARATUS FOR FORMING GASEOUS MIXTURES

The present invention relates to a method and apparatus for forming gaseous mixtures.

The gaseous mixtures formed according to the present invention have utility in the field of therapy, for example by administration by gas inhalation or other therapeutic techniques, as well as in a variety of industrial applications.

Briefly stated, the present invention comprises a method and apparatus, in which gas is introduced into a gas-tight container which has first been purged by a suitable gas, the gas being introduced into the container from at least two sources according to a predetermined ratio of the gases to each other, such as 1:10, 1:100, etc.

The gas is then mixed in the container, for example for about 5 minutes, by agitation, heating the container, or circulation externally of the container and back into the container through a pump.

A second dilution can then be carried out, in the same or a separate container, by introducing the gas diluted in the first stage, into the same or a further gas-tight container, with the same or a different ratio of dilution. Further dilutions can be effected as desired, according to a tenfold or other selected ratio, to form with accuracy and precision a gaseous mixture as dilute in one or more of the components, as is desired.

The gaseous mixtures thus formed, can be applied directly in industrial processes or medical therapies, or can be stored in suitable containers, at atmospheric or elevated pressure.

The gases can be introduced into the gas-tight container, either in liquid or in gaseous phase. If in liquid phase, they are vaporized downstream of the container prior to dispensing the gaseous mixture.

Other features and advantages of the present invention will become apparent from a consideration of the following description, taken in connection with the accompanying drawing, which is a schematic diagram of one embodiment of apparatus according to the present invention for practicing the method of the present invention.

Referring now to the drawing in greater detail, there is shown a fluid-tight container 1 which, prior to use, will be purged with a suitable gas, preferably the diluent gas subsequently to be used. Into container 1 is introduced a plurality of different gases from respective sources 2 thereof, by means of connections 3 such as valves or the like.

The gases are introduced according to a predetermined ratio to each other: for example 1:10, and are then mixed together, either in liquid phase or in vapor phase. Preferably, this mixing takes place for about 5 minutes, and can be effected by providing an agitator (not shown) within container 1 or means (not shown) for heating container 1. In the illustrated embodiment, however, this mixing is effected by means of a circulation pump 4 disposed outside container 1, through which the gaseous mixture is circulated and recirculated as necessary in a closed cycle, so as to achieve complete mixing.

Upon withdrawal of a suitable quantity of the gas from container 1, or upon transfer of this gas to a further container, a further dilution can be achieved by using a predetermined portion of the gaseous mixture initially formed in container 1, in combination with a further quantity of the diluent gas, so as to achieve, for example, in the case of a gas which was first diluted 1:10, a further dilution to a ratio of 1:100. By the same technique, further dilutions can be effectuated, to achieve with precision and accuracy any desired dilution of one gas in another or others.

The gaseous mixture thus finally formed, will be withdrawn from container 1 via connection 5 in the form of a valve or the like.

The sources of gas can be as desired, and can comprise gases formed by various techniques such as decomposition, distillation, fermentation, combustion, evaporation, sublimation or the like.

Similarly, the individual gases to be mixed can have any desired chemical nature and can comprise, for example, mixtures in the proportion of 1:10 or 1:100 of oxygen in carbon dioxide, oxygen in nitrogen, or ammonia in nitrogen, oxygen, hydrogen or the like.

Although the present invention has been described and illustrated in connection with preferred embodiments, it is to be understood that modifications and variations may be resorted to, without departing from the scope of the invention, as those skilled in this art will readily understand. Such modifications and variations are considered to be within the purview of the present invention as defined by the appended claims.

What is claimed is:

1. A process for the production of gaseous mixtures, comprising introducing into a closed container a mixture of gases having a predetermined ratio to each other, with one gas in lesser quantity than another gas, thoroughly mixing the first gaseous mixture thus produced, then subjecting said first gaseous mixture, with said gases in the same said predetermined ratio, to a further dilution with an accurately predetermined quantity of said another gas, and thoroughly mixing the second gaseous mixture thus produced, thereby to produce a said second gaseous mixture in which said one gas is present in highly diluted condition but accurately predetermined quantity.

2. A process as claimed in claim 1, and purging said closed container with said another gas prior to introduction of said mixture of gases thereinto.

3. A process as claimed in claim 1, and effecting said further dilution in a container other than said closed container.

* * * * *